(12) United States Patent
Power et al.

(10) Patent No.: US 10,960,154 B2
(45) Date of Patent: Mar. 30, 2021

(54) AEROSOL DEVICE

(71) Applicant: NORTON (WATERFORD) LIMITED, Waterford (IE)

(72) Inventors: James Noel Power, Waterford (IE); Simon Kaar, Cork (IE); Andrew Gibbs, West Midlands (GB)

(73) Assignee: Norton (Waterford) Limited

( * ) Notice: Subject to any disclaimer, the term of this patent is extended or adjusted under 35 U.S.C. 154(b) by 1067 days.

(21) Appl. No.: 15/309,538

(22) PCT Filed: May 13, 2015

(86) PCT No.: PCT/EP2015/060663
§ 371 (c)(1),
(2) Date: Nov. 8, 2016

(87) PCT Pub. No.: WO2015/169974
PCT Pub. Date: Nov. 12, 2015

(65) Prior Publication Data
US 2017/0189630 A1    Jul. 6, 2017

(30) Foreign Application Priority Data

May 9, 2014   (GB) ..................................... 1408229

(51) Int. Cl.
*A61M 15/00*    (2006.01)
*A61M 15/08*    (2006.01)
(Continued)

(52) U.S. Cl.
CPC .......... *A61M 15/009* (2013.01); *A61M 11/08* (2013.01); *A61M 15/08* (2013.01);
(Continued)

(58) Field of Classification Search
CPC .... A61M 11/00–003; A61M 11/06–08; A61M 15/009
See application file for complete search history.

(56) References Cited

U.S. PATENT DOCUMENTS

| | | | |
|---|---|---|---|
| 5,899,201 A | 5/1999 | Schultz et al. | |
| 2003/0089368 A1* | 5/2003 | Zhao ................... | A61M 15/009 128/200.23 |

(Continued)

FOREIGN PATENT DOCUMENTS

| | | |
|---|---|---|
| WO | WO9947195 A1 | 9/1999 |
| WO | WO0243794 A1 | 6/2002 |

(Continued)

*Primary Examiner* — Rachel T Sippel
(74) *Attorney, Agent, or Firm* — BakerHostetler

(57) ABSTRACT

The present invention provides an aerosol device for delivering a pharmaceutical formulation by inhalation via the mouth to the lungs or to the nostril in metered doses comprising: a pressurised aerosol canister including a vial containing a pharmaceutical formulation comprising an active ingredient, a propellant and, optionally, a co-solvent, the aerosol canister further comprising a metering valve having a valve stem; and an actuator for the aerosol canister, the actuator including a delivery outlet and a stem block, the stem block having a receptacle into which the valve stem of the metering valve of the aerosol canister is received and axially located and being displaceable relative to the vial of the aerosol canister to actuate the metering valve of the aerosol canister, a sump extending below the receptacle, the stem block further defining a discharge orifice arranged to direct the pharmaceutical formulation through the delivery outlet, a transfer tunnel having an input opening and an output opening through which a dispensed dose of the pharmaceutical formulation is able to pass from the sump to the discharge orifice, and a land length defining the distance from between the input opening and output opening, (Continued)

wherein the input opening and the output opening have cross-sectional areas of from 0.002 to 0.8 mm$^2$ and the cross-sectional area of the input opening is smaller than the cross-sectional area of the output opening, and wherein the land length is from 0.5 mm to 10 mm.

12 Claims, 5 Drawing Sheets

(51) Int. Cl.
    *B65D 83/20*     (2006.01)
    *B65D 83/28*     (2006.01)
    *B65D 83/54*     (2006.01)
    *A61M 11/08*     (2006.01)

(52) U.S. Cl.
    CPC ........... *B65D 83/205* (2013.01); *B65D 83/28* (2013.01); *B65D 83/54* (2013.01)

(56) References Cited

U.S. PATENT DOCUMENTS

| | | | |
|---|---|---|---|
| 2012/0085345 A1 | 4/2012 | Zeng et al. | |
| 2012/0180785 A1* | 7/2012 | Trill | A61M 15/009 128/200.23 |
| 2014/0060531 A1* | 3/2014 | Brambilla | A61M 15/0065 128/203.12 |
| 2014/0299128 A1* | 10/2014 | Jinks | A61M 15/009 128/203.15 |

FOREIGN PATENT DOCUMENTS

| | | |
|---|---|---|
| WO | WO2004041326 A2 | 5/2004 |
| WO | WO2008024728 A2 | 2/2008 |
| WO | WO2013083569 A1 | 6/2013 |

* cited by examiner

AEROSOL DEVICE

CROSS-REFERENCE TO RELATED APPLICATIONS

This application is the National Stage of International Patent Application No. PCT/EP2015/060663, filed May 13, 2015, which claims the benefit of GB Patent Application No. 1408229.1, filed May 9, 2014, the disclosures of which are incorporated herein by reference in their entireties.

This invention relates to an aerosol device and particularly to an aerosol device for delivery of a pharmaceutical formulation to the lungs or nostril.

Aerosol devices for the delivery of medicament to the lungs or nostril can be useful for the prophylaxis and/or treatment of certain diseases and disorders of the respiratory tract, diseases and disorders of nostril or systemic diseases.

Aerosol devices include an aerosol canister comprising a vial (usually cylindrical) containing a medicament. The medicament is typically an active ingredient together with a suitable propellant. The medicament may be in the form of a solution formulation or a suspension formulation in the propellant and excipients may be added to facilitate dissolution of the active ingredient (e.g. co-solvents) or to stabilise the suspension (e.g. surfactants). The vial is provided with a metering valve having an axially extending valve stem. Displacement of the valve stem relative to the vial causes the dispensation of a dose of the medicament formulation as an aerosol.

Such aerosol canisters also comprise an actuator which comprises a delivery outlet and a stem block, the stem block having a discharge orifice through which the medicament can exit into the mouth or nostril.

The discharge orifice of the aerosol device is narrow enough so that it can fit into the mouth or nostril.

It is desirable for the spray force of the medicament which exits the aerosol device to be low (i.e. a soft plume is desired) as a soft plume provides comfort to the user of the device. It is also desirable for the plume of medicament to be narrow so that the medicament plume cannot be retained on the surfaces of the actuator and fits through a mouth or nose piece.

There remains a need in the art for an aerosol device for the delivery of a medicament to the lungs or nostril that is able to deliver soft and narrow plume characteristics.

Accordingly, the present invention provides an aerosol device for delivering a pharmaceutical formulation by inhalation via the mouth to the lungs or to the nostril in metered doses comprising: a pressurised aerosol canister including a vial containing a pharmaceutical formulation comprising an active ingredient, a propellant and, optionally, a co-solvent, the aerosol canister further comprising a metering valve having a valve stem; and an actuator for the aerosol canister, the actuator including a delivery outlet and a stem block, the stem block having a receptacle into which the valve stem of the metering valve of the aerosol canister is received and axially located and being displaceable relative to the vial of the aerosol canister to actuate the metering valve of the aerosol canister, a sump extending below the receptacle, the stem block further defining a discharge orifice arranged to direct the pharmaceutical formulation through the delivery outlet, a transfer tunnel having an input opening and an output opening through which a dispensed dose of the pharmaceutical formulation is able to pass from the sump to the discharge orifice, and a land length defining the distance from between the input opening and output opening, wherein the input opening and the output opening have cross-sectional areas of from 0.002 to 0.8 mm$^2$ and the cross-sectional area of the input opening is smaller than the cross-sectional area of the output opening, and wherein the land length is from 0.5 mm to 10 mm.

The present invention will now be described with reference to the accompanying drawings, in which.

Figure 1:
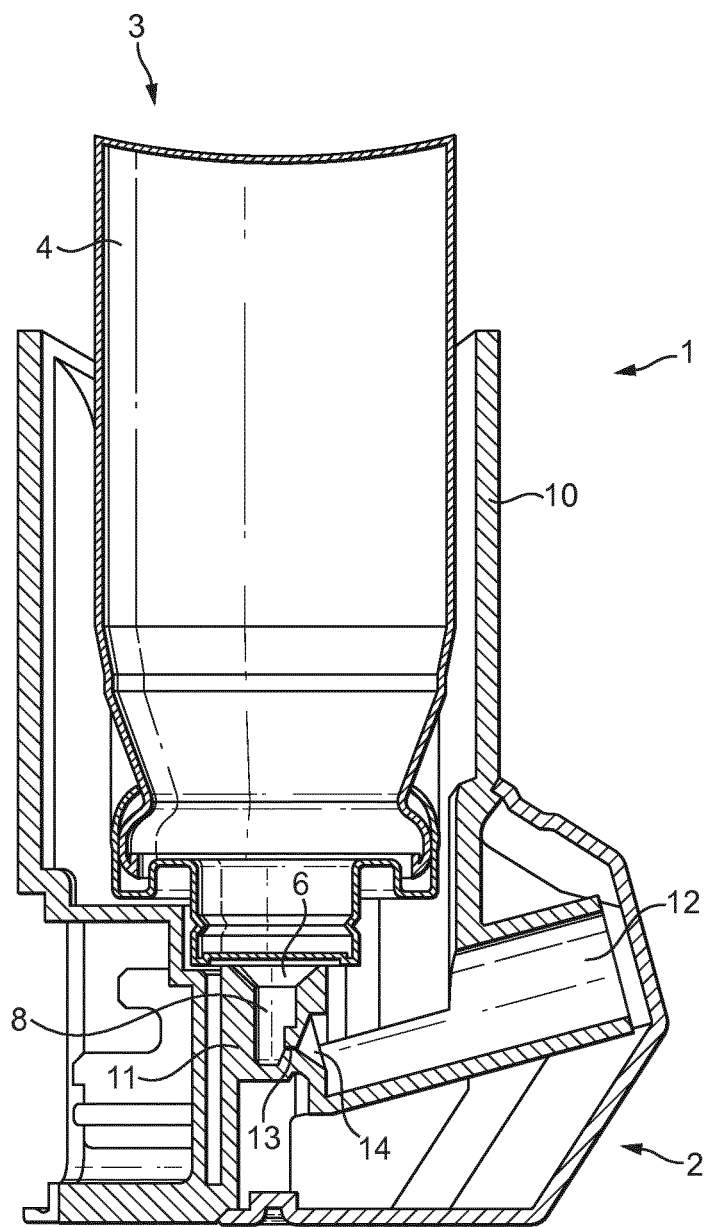
FIG. 1 shows an aerosol device according to the present invention.

The aerosol device of the present invention may be used in the treatment of diseases and disorders of the nostril, diseases and disorders of the respiratory tract, or systemic diseases. Examples include rhinitis (e.g. allergic rhinitis), asthma and COPD.

The aerosol device of the present invention contains a pharmaceutical formulation. The pharmaceutical formulation comprises an active ingredient and a propellant. In principle, any pharmaceutically active ingredient that is soluble or suspended in the formulation and acts via the lungs or nasal cavity may be used in the present invention. The active ingredient is present in the formulation of the invention in a therapeutically effective amount, i.e. an amount such that metered volumes of the medicament administered to the patient contains an amount of drug effective to exert the intended therapeutic action. The formulation according to the present invention may be a solution formulation or a suspension formulation.

Non-limiting examples of the active ingredient which may be used in the formulation of the present invention are as follows.

(i) Steroids, such as alcometasone, beclomethasone, betamethasone, budesonide, ciclesonide, clobetasol, deflazacort, diflucortolone, desoxymethasone, dexamethasone, fludrocortisone, flunisolide, fluocinolone, fluometholone, fluticasone, hydrocortisone, mometasone furoate, nandrolone decanoate, neomycin sulfate, rimexolone, methylprednisolone, prednisolone and triamcinolone acetonide. The steroid is preferably beclomethasone dipropionate, budesonide, fluticasone propionate or mometasone furoate. Beclomethasone dipropionate (also termed beclometasone dipropionate (INN) or (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phen-anthren-17-yl propionate (IUPAC)) is particularly preferred.

(ii) Short- and long-acting $\beta_2$-adrenergic agonists. Long-acting $\beta_2$-agonists (LABAs) include formoterol, salmeterol, indacaterol, carmoterol and salts thereof, such as formoterol fumarate and salmeterol xinafoate. Short-acting $\beta_2$-agonists include salbutamol, terbutaline and salts thereof such as salbutamol sulfate.

(iii) Anticholinergics, such as muscarinic receptor antagonists, e.g. dexpyrronium, glycopyrronium, ipratropium, oxitropium, tiotropium, trospium, tolterodine, solifenacin, darifenacin, aclidinium and fesoterodine.

(iv) Antihistamines, such as azelastine, desloratadine, fexofenadine, levocetirizine and olopatadine.

(v) Other drugs, such as ACE inhibitors, acetylcholinesterase inhibitors, alpha-blockers, analgesics, e.g. opioids, angiotension II receptor blockers, antiarrhythmics, antibiotics, anti-cancer agents, anti-clotting agents, antidepressants, anti-emetics, anti-fungal drugs, anti-inflammatory agents, antipsychotics, anti-viral agents, bisphosphonates, calcium channel blockers, diuretics, dopamine agonists, hormonal drugs, hypoglycaemics, immunoglobulins, leukotriene receptor antagonists, local anaesthetics, mucolytic agents, narcotic agonists and opiate antidotes, nitrates, NMDA receptor antagonists, nucleic acids, phosphodiesterase 4 (PDE4) inhibitors, polypeptides, potassium channel modulators, serotonin agonists, serotonin antagonists, smoking cessation drugs and sympathomimetic drugs.

The active ingredient which may be used in the formulation of the present invention is preferably selected from beclomethasone dipropionate, budesonide, fluticasone propionate and mometasone furoate. Beclomethasone dipropionate is particularly preferred.

A therapeutically effective amount of the active ingredient needs to be delivered and this amount will vary depending on the nature of the active ingredient. A typical range is 1 µg to 1 mg. In a preferred embodiment, the aerosol device of the present invention provides a delivered dose of the active ingredient of at least 50 µg, more preferably at least 60 µg and most preferably at least 70 µg, while at the same time providing the desirable plume characteristics.

The aerosol device of the present invention also contains a propellant. Preferably, the propellant is a hydrofluoroalkane (HFA) propellant, more preferably P134a (1,1,1,2-tetrafluoroethane), P227 (1,1,1,2,3,3,3-heptafluoropropane) or mixtures thereof. Other hydrofluorocarbons, hydrocarbons or aliphatic gases (e.g. butane or dimethylether) may be added to modify the propellant characteristics as required. However, it is preferred that P134a and/or P227 are the sole propellants present. The propellant preferably constitutes 80% to 99% w/w, more preferably 90 to 98% w/w, based on the total weight of the formulation.

The present invention is applicable to aerosol devices for delivering all types of pharmaceutical formulations, but is particularly effective for delivering pharmaceutical formulations including a co-solvent for the active ingredient. The co-solvent is generally present in order to solubilise the active ingredient and the precise nature of the co-solvent will therefore depend on the nature of the active ingredient. However, the co-solvent is preferably a C2-6 aliphatic alcohol, such as ethanol or propylene glycol, and preferably ethanol. When required, the co-solvent is present in an amount sufficient to dissolve substantially all of the medicament present in the formulation and to maintain the medicament dissolved over the time period and conditions experienced by commercial aerosol products. Preferably the solvent is present in an amount to prevent precipitation of the active ingredient even at temperatures down to −20° C. The solvent is preferably anhydrous, although trace amounts of water absorbed by the ingredients, for example during manufacture of the medicament, may be tolerated. Anhydrous ethanol is particularly preferred. The co-solvent, preferably ethanol, is typically present at 1-20% w/w, more preferably 6-15% w/w and most preferably about 8% w/w, based on the total weight of the formulation.

The pharmaceutical formulation of the present invention is preferably substantially free of surfactant. Surfactants are often added to suspensions to stabilise the suspension. However, when the formulation of the present invention is a solution, a surfactant is not required. Nevertheless, small quantities can be tolerated without adversely affecting the formulation. Preferably the formulation contains no more than 0.0005% w/w of a surfactant based on the total weight of the formulation. Preferred formulations contain no surfactant.

The pharmaceutical formulation of the present invention may be prepared by dissolving the desired amount of active ingredient in the desired amount of co-solvent accompanied by stirring or sonication. The aerosol canister may then be filled using conventional cold-fill or pressure-fill methods.

Figure 2:
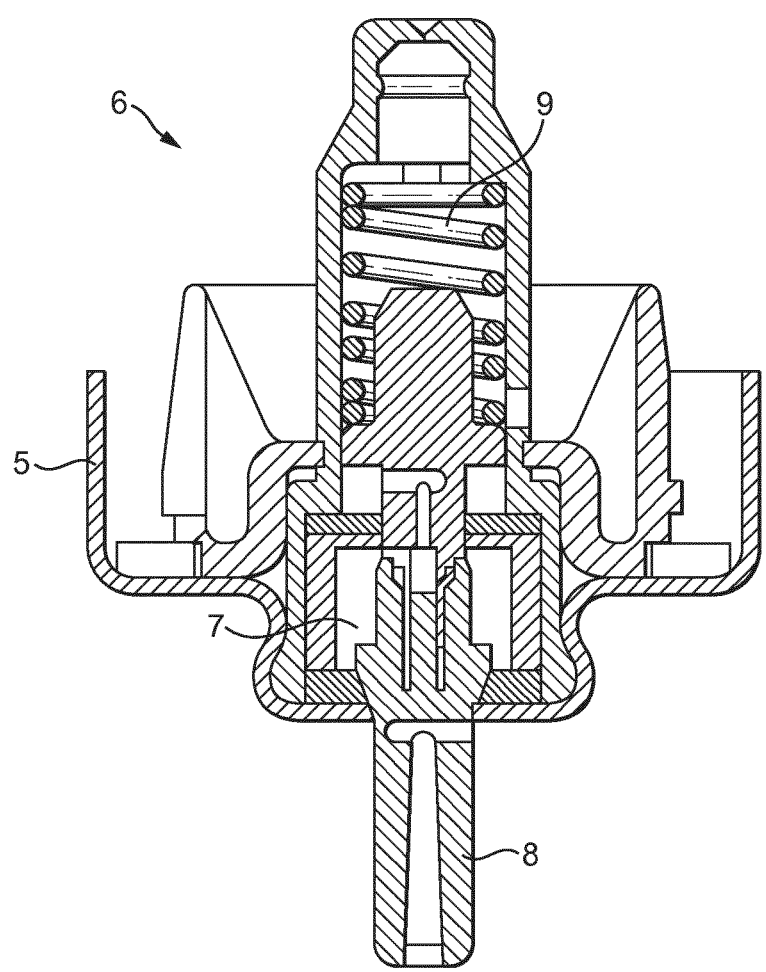
FIG. 2 shows a conventional valve for a pressurised metered dose inhaler (pMDI)

With reference to FIG. 1 and FIG. 2 (FIG. 2 is reproduced from WO 99/47195), an aerosol device 1 according to the present invention is based on a conventional pMDI. Accordingly, the device 1 comprises an actuator 2 accommodating the pressurised aerosol canister 3 containing a pharmaceutical formulation for delivery by inhalation via the mouth to the lungs or to the nostril of the user.

Such aerosol canisters 3 are known in the art and are commercially available. The aerosol canister 3 is typically composed of aluminium or an aluminium alloy. The internal surfaces of the aerosol canister 3 may be coated with a fluorocarbon polymer, such as PTFE or FEP, optionally together with non-fluorinated polymer to promote adhesion, such as PES.

The aerosol canister 3 is constructed to a standard design and specification and comprises a substantially cylindrical vial body 4 which contains the pharmaceutical formulation. The pharmaceutical formulation comprises an active ingredient and a propellant and, optionally, a co-solvent.

The aerosol canister 3 is charged with a pharmaceutical formulation as described hereinabove. The vial body 4 is provided with a ferrule 5 which is crimped over a lip of the body to seal hermetically the pharmaceutical formulation under pressure.

The ferrule 5 of the aerosol canister 3 is provided with a metering valve 6 designed to deliver a metered amount of the pharmaceutical formulation to the user for each actuation of the valve 6. The metering valve 6 is of a known type available from manufacturers such as Consort Medical plc and 3M Drug Delivery Systems. See WO 99/47195 for further details of the metering valve suitable for use in the device of the present invention. The valve 6 generally comprises a metering chamber 7 and a valve stem 8 in the form of a narrow tube protruding outwardly from ferrule 5. The valve stem 8 is axially displaceable relative to the vial 4 to cause the dispensation of a metered dose of the pharmaceutical formulation through the valve stem 8. The metering valve 6 is actuated by displacing the valve stem 8 into the valve body against the action of a valve spring 9 to allow the metered amount of the pharmaceutical formulation to vent from the metering chamber through the stem 8. The propellant component of the pharmaceutical formulation causes atomisation of the active ingredient by vaporising on release to the atmosphere. The metering chamber 7 is then recharged with the pharmaceutical formulation as the valve stem 8 is allowed to return to its starting position under the action of the valve spring 9.

With further reference to FIG. 1, the aerosol canister 3 is received into the open end of a body 10 of the actuator 2, with the valve stem 8 being received into and axially located by a stem block 11 of the actuator 2. The actuator body 10 is a moulded plastics component and the stem block 11 is formed as a protrusion which stands from the closed end of the actuator body 10. The stem block 11 has a receptacle (usually cylindrical) into which the valve stem 8 of the aerosol canister 3 is received and axially located. The receptacle is configured for an interference fit with the valve stem 8.

The actuator body 10 generally defines a sleeve-like portion having a substantially circular cross-section, within which sleeve-like portion the aerosol canister 3 is axially displaceable relative to the stem block 11 and valve stem 8 to actuate the metering valve 6. A portion of the aerosol canister 3 at its non-valve end remains exposed in use so that the user is able to apply a manual pressure to displace the aerosol canister relative to the valve stem.

The stem block 11 is moulded with a discharge orifice 14 facing the delivery outlet, and the discharge orifice 14 is fluidly connected to the receptacle of the stem block so that the pharmaceutical formulation is able to pass from the aerosol canister, through the stem block discharge orifice 14 and delivery outlet 12 and into the lungs or nostril. The delivery outlet 12 directly faces the stem block discharge orifice 14 so that an aerosol plume produced at the valve stem 8 can be delivered through the stem block discharge orifice 14 and delivery outlet 12 into the lungs or nostril. The discharge orifice is therefore arranged to direct the aerosol plume through the delivery outlet.

Although similar in the above-described respects, the aerosol device 1 according to the present invention differs from conventional pMDIs in the following respect.

The aerosol device 1 according to the present invention differs from conventional pMDIs in relation to the design of the stem block 11, in particular the transfer tunnel 13. A stem block of a conventional pMDI is moulded with a discharge orifice facing the delivery outlet, and the discharge orifice is fluidly connected to the receptacle of the stem block so that the pharmaceutical formulation is able to pass from the aerosol canister and through the delivery outlet. By comparison, the aerosol device 1 according to the present invention has a stem block 11 that is provided with a transfer tunnel 13 through which the pharmaceutical formulation is able to pass from the aerosol canister 3, through the transfer tunnel 13, discharge orifice 14 and delivery outlet 12 and into the lungs or nostril of the user.

It has been found that the dimensions of the transfer tunnel 13 affect the properties of the spray plume expelled from the aerosol device 1. Specifically, it has been found that the longer the land length of the transfer tunnel 13 the narrower the plume (where the land length defines the distance from between the input opening and the output opening). In addition, it has been found that the larger the cross-sectional area of the transfer tunnel 13, the narrower the plume. It has also been found that the smaller the cross-sectional area of the transfer tunnel 13, the lower the spray force plume (i.e. the softer the plume).

A soft plume is desirable because it provides good patient tolerability insofar as the spray plume is comfortable for the user. By soft plume it is meant that the spray force of the plume is less than 40 mN. In addition, a soft plume can be described as a plume which has a long duration, i.e. the longer the plume duration the softer the plume. Spray force values are measured under controlled conditions of temperature of 25° C., pressure of 101 KPa and relative humidity of 50%. The impaction plate is mounted in a vertical orientation. The aerosol device is mounted in the movable carriage so that the discharge orifice of the device is positioned 30 mm from the impaction plate. The aerosol device is then actuated and the maximum compression force of the impaction plate recorded. Six actuations are measured for each device to be tested. The mean of these six values is recorded as the spray force value for the device. The measurements are preferably taken using an actuation velocity of 70 mm/s and an acceleration of 7,000 mm/s$^2$, although this is not critical as the spray force is not significantly affected by these variables.

A narrow plume (also known as a focused plume) is also desirable for an aerosol device to ensure that a large proportion of the dose is delivered to the lungs or nostril of the user and not retained on the surfaces of the actuator. In addition, the plume must be narrow so that it can fit through the narrow delivery outlet. This is especially important when delivery is to the nostril as the delivery outlet is smaller.

Surprisingly, the present inventors have found that a transfer tunnel having an input opening and an output opening, the input opening being smaller than the output opening and the input opening and the output opening having cross-sectional areas of from 0.002 to 0.8 mm$^2$ and the land length of the transfer tunnel being from 0.5 mm to 10 mm, gives rise to a spray plume which is narrow and which has a low spray force (soft plume). In addition, a transfer tunnel of this type has been found to be less prone to blockages than a cylindrical shaped transfer tunnel. It is surprising that this unusual transfer tunnel design gives rise to a narrow and soft plume, as this contradicts with the results obtained for a cylindrical shaped transfer tunnel. The transfer tunnel input opening and output openings are in fluid communication.

Figure 3:
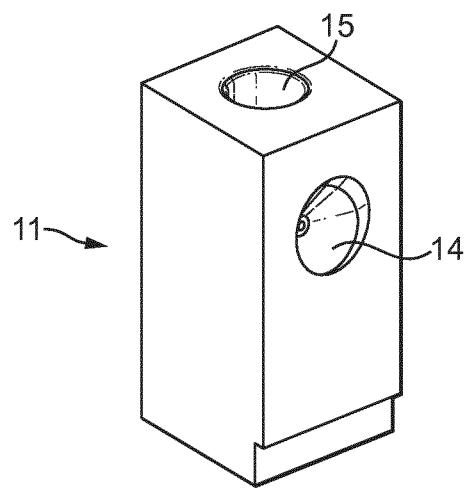
FIG. 3 shows a stem block discharge orifice according to the present invention.

FIG. 3 shows the stem block 11 according to the present invention comprising a receptacle 15 into which the valve stem 8 of metering valve of the aerosol canister is received and axially located and the discharge orifice 14.

Figure 4:
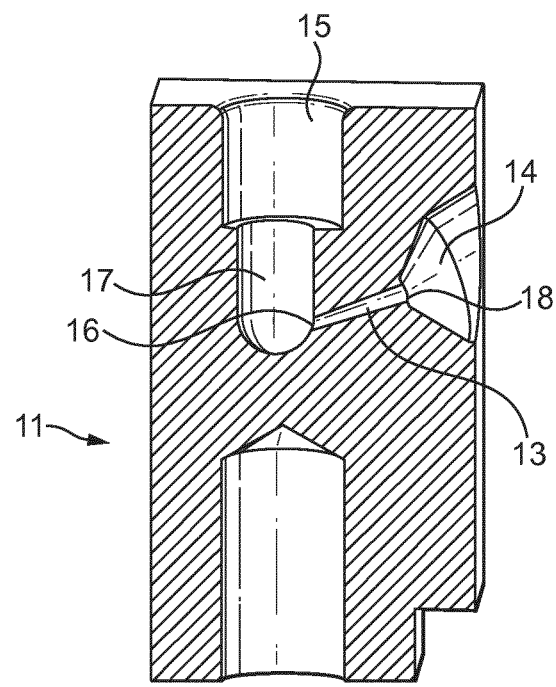
FIG. 4 shows a cut-away perspective schematic view of the stem block discharge orifice of FIG. 3.

FIG. 4 is a view similar to that of FIG. 3, but with half of the stem block 11 cut-away to show the inside of the stem block 11. It can be seen that the stem block 11 also comprises a sump 17 which is narrower than the receptacle of the stem block 15 in order to locate axially the valve stem 8 of the canister (valve stem 8 is not shown in FIG. 3). The stem block 11 is shown having the transfer tunnel 13 extending from the sump 17 to the discharge orifice 14. The transfer tunnel 13 defines a passage from the sump 17 to the discharge orifice 14. That is, the transfer tunnel 13 is in fluid communication with the sump 17 and the discharge orifice 14 of the stem block 11. The delivery outlet, the stem block discharge orifice 14 and the transfer tunnel 13 may be aligned with each other, that is to say they may have substantially identical axes. Thus, on actuation, the pharmaceutical formulation is able to pass from the aerosol canister 3, through the sump 17, transfer tunnel 13, discharge orifice 14 and delivery outlet 12, and into the lungs or nostril of the user.

Figure 5:
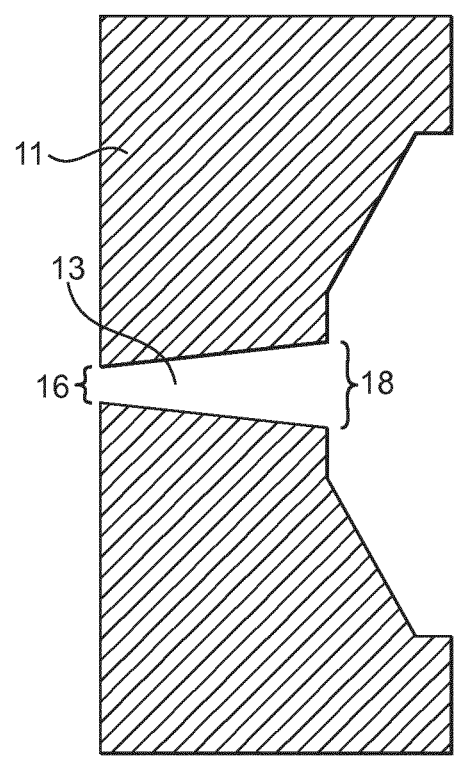
FIG. 5 shows an expanded view of the transfer tunnel according to the present invention.

The cross-sectional area of the transfer tunnel output opening 18 is larger than the cross-sectional area of the transfer tunnel input opening 16. By this it is meant that the cross-sectional area of the output opening is greater than the cross-sectional area of the input opening (which may be defined, for example, in mm$^2$). This can be seen in FIGS. 3 to 5.

It has been found that the ratio of the cross-sectional area of the input opening 16 to the output opening 18 has a significant effect on the spray characteristics of the aerosol device. In one embodiment, the ratio of the cross-sectional area of the input opening 16 to the cross-sectional area of the output opening 18 is from 0.1:1 to 0.9:1, preferably 0.2:1 to 0.5:1 and most preferably 0.3:1 to 0.4:1 (e.g. 0.36:1).

The transfer tunnel input and output openings have cross-sectional areas of from 0.002 to 0.8 mm$^2$, preferably 0.01 to 0.6 mm$^2$ and most preferably 0.03 to 0.4 mm$^2$ (e.g. the cross-sectional area of the input opening 16 is 0.07 mm² and the cross-sectional area of the output opening 18 is 0.20 mm²).

A transfer tunnel cross-sectional area which falls outside this range provides a spray plume which does not have the desired characteristics for use in the aerosol device.

The land length of the transfer tunnel 13 is from 0.5 to 10 mm. Preferably, the land length of the transfer tunnel 13 is from 1 to 8 mm and most preferably from 1 to 5 mm (e.g. 2.5 mm). The land length of the transfer tunnel is the distance from the input opening to the output opening of the transfer tunnel.

The cross-sectional area of the transfer tunnel 13 may increase either continuously or non-continuously from the input opening 16 to the output opening 18. Preferably, the cross-sectional area of the transfer tunnel 13 increases continuously from the input opening 16 to the output opening 18 (put another way, it tapers from the output opening 18 to the input opening 16).

The cross-section of the input and output openings of the transfer tunnel 13 may be any shape. Preferably, the input and output openings are circular (i.e. in cross-section). When the cross-sectional shape is circular, the transfer tunnel 13 is defined by its length and diameter.

The transfer tunnel 13 may be any shape such that the output opening 18 is larger than the input opening 16. Preferred shapes of the transfer tunnel include a truncated cone, a truncated pyramid (e.g. a square-, pentagonal-, hexagonal- or star-based pyramid), a stepped truncated cone or a stepped truncated pyramid (e.g. a square-, pentagonal-, hexagonal- or star-based pyramid). A particularly preferred shape for the transfer tunnel 13 is a truncated cone, i.e. where the cross-sectional area of the transfer tunnel 13 increases continuously from the input opening 16 to the output opening 18 and both the input and output openings 16,18 are circular.

With reference to FIG. 1 and FIG. 4, before application of the aerosol device 1 described hereinabove, the user shakes the device 1 several times, as is normal practice for pMDIs. To use the device 1, the user inserts the delivery outlet 12 into a mouth or nostril and depresses the exposed end of the aerosol canister 3. Displacement of the canister 3 relative to the valve stem 8 causes actuation of the metering valve 6 and a metered amount of the pharmaceutical formulation is vented from the metering chamber in the aerosol canister 3. The formulation passes through the sump 17 and into the transfer tunnel 13 before finally being discharged through the discharge orifice 14 and the delivery outlet 12.

The present invention may be for delivery of atomised pharmaceutical formulation by inhalation via the mouth to the lungs or to the nostril.

When delivery is for the nostril, the aerosol device is a nasal spray device and delivery outlet 12 is a nose piece. The delivery outlet may be a tubular nose piece adapted for insertion into the nostril, and a circular end of the nose piece may have an inner diameter of 5 to 7.5 mm (e.g. about 7.2 mm). The delivery outlet, the stem block discharge orifice 14 and the transfer tunnel 13 may be aligned with each other, that is to say they may have substantially identical axes. The axis of the delivery outlet may be substantially perpendicular, or at an angle of up to 20° to the perpendicular, to the aerosol canister and the receptacle of the stem block 11. Preferably an axis of the nose piece defines an angle of about 80° with the sleeve-like portion of the actuator body 10. The nose piece directly faces the stem block 11 so that an aerosol plume produced at the valve stem 8 can be delivered through stem block discharge orifice 14 through the nose piece and into the nostril.

Nasal spray devices are for the delivery of medicament to the nostril, particularly the nasal mucosa. Such devices are also capable of delivering medicament to the systemic circulation via the turbinates and lymphoid tissues located at the back of the nostril and to the central nervous system via the olfactory region at the top of the nostril.

When delivery is for the lungs, the delivery outlet 12 is a mouth piece. Such mouth pieces are well known in the art. See, for example, Pharmaceutics—The Science of Dosage Form Design, Second Edition, Ed. M. E. Aulton, Churchill Livingstone, 2002, page 476 et seq for details.

The present invention will now be discussed with reference to the examples, which are not intended to be limiting.

EXAMPLE

Example

Plume width values were measured for conventional aerosol device s and aerosol device s according to the present invention, at different distances from the discharge orifice using a variety of transfer tunnels of differing dimensions and shapes. In addition, plume duration values were measured for the aerosol device according to the present invention using a variety of transfer tunnels of differing dimensions and shapes.

The devices tested are summarised in Table 1

TABLE 1

| Entry | Input opening diameter (mm) | Input opening cross-sectional area (mm²) | Output opening diameter (mm) | Output opening cross-sectional area (mm²) | Orifice length (mm) |
|---|---|---|---|---|---|
| 1 | 0.3 | 0.07 | 0.3 | 0.07 | 1.5 |
| 2 | 0.3 | 0.07 | 0.3 | 0.07 | 2.0 |
| 3 | 0.3 | 0.07 | 0.3 | 0.07 | 2.5 |
| 4 | 0.3 | 0.07 | 0.3 | 0.07 | 2.5 |
| 5 | 0.4 | 0.13 | 0.4 | 0.13 | 1.5 |
| 6 | 0.4 | 0.13 | 0.4 | 0.13 | 2.0 |
| 7 | 0.4 | 0.13 | 0.4 | 0.13 | 2.5 |
| 8 | 0.5 | 0.20 | 0.5 | 0.20 | 1.5 |
| 9 | 0.5 | 0.20 | 0.5 | 0.20 | 2.0 |
| 10 | 0.5 | 0.20 | 0.5 | 0.20 | 2.5 |
| 11 | 0.3 | 0.07 | 0.5 | 0.20 | 2.5 |
| 12 | 0.3 | 0.07 | 0.5 | 0.20 | 2.5 |

The device was loaded with an aerosol canister containing a placebo formulation. The placebo formulation contained an HFA propellant. The aerosol device according to the present invention was actuated for the tests using a SprayVIEW® system, which is available from Proveris Scientific Corporation, Marlborough, Mass., USA. The results are set out in FIG. 6.

Figure 6:
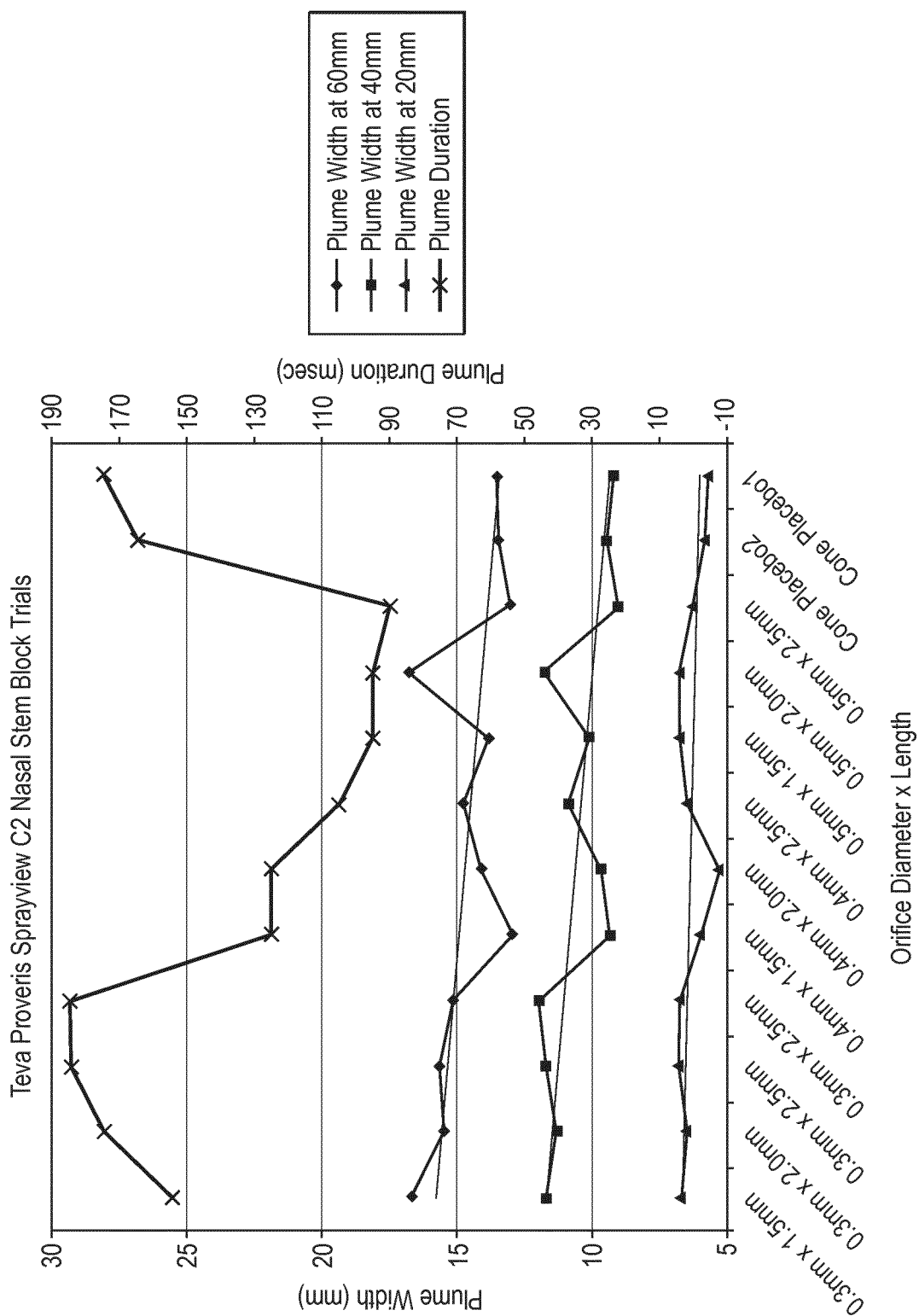
FIG. 6 is a graph showing the effect on plume width and plume duration for different discharge orifices.

It can be seen from Table 1 and FIG. 6 that when the transfer tunnel input opening diameter and the output opening diameter are equal (Entries 1-10) the plume duration is highest where the opening diameters are small (i.e. Entries 1-4). However, the plume width is lowest for larger opening diameters (i.e. Entries 8-10). It can also be seen from FIG. 6 that when the input opening diameter and the output opening diameter are not equal (Entries 11 and 12) the plume duration is high and similar to the plume duration obtained for discharge orifices where the diameters of the input and output openings are equal and small (i.e. Entries 1-4). In addition, the plume width for the discharge orifices of Entries 11 and 12 are small and similar to that obtained for the discharge orifices where the diameters of the input and output openings are equal and large (i.e. Entries 8-10). Accordingly, the aerosol device according to the present invention provides the advantage in that it achieves both large plume duration (i.e. a soft plume) and a small (i.e. narrow) plume width.

The invention claimed is:

1. An aerosol device for delivering a pharmaceutical formulation by inhalation via the mouth to the lungs or to a nostril of a patient in metered doses comprising:
   a pressurised aerosol canister including a vial containing a pharmaceutical formulation comprising an active ingredient and a propellant, the aerosol canister further comprising a metering valve having a valve stem; and
   an actuator for the aerosol canister, the actuator including a delivery outlet and a stem block, the stem block having a receptacle into which the valve stem of the metering valve of the aerosol canister is received and axially located and being displaceable relative to the vial of the aerosol canister to actuate the metering valve of the aerosol canister, a sump extending below the receptacle, the stem block further defining a discharge orifice arranged to direct the pharmaceutical formulation through the delivery outlet, a transfer tunnel having an input opening and an output opening through which a dispensed dose of the pharmaceutical formulation is able to pass from the sump to the discharge orifice, and a land length defining the distance between the input opening and the output opening,
   wherein the input opening and the output opening have cross-sectional areas of from 0.002 to 0.8 $mm^2$ and the cross-sectional area of the input opening is smaller than the cross-sectional area of the output opening, and
   wherein the land length is from 1 mm to 8 mm.

2. The device as claimed in claim 1, wherein the ratio of the cross-sectional area of the input opening to the cross-sectional area of the output opening is from 0.1:1 to 0.9:1.

3. The device as claimed in claim 1, wherein the input opening and the output opening have cross-sectional areas of from 0.01 to 0.6 $mm^2$.

4. The device as claimed in claim 1, wherein the cross-sectional area of the transfer tunnel increases continuously from the input opening to the output opening.

5. The device as claimed in claim 1, wherein the input opening and the output opening are circular.

6. The device as claimed in claim 4, wherein the transfer tunnel is a truncated cone.

7. The device as claimed in claim 1, wherein the delivery outlet is a nose piece and the delivery of the pharmaceutical formulation is for delivery to the nostril.

8. The device as claimed in claim 1, wherein the pharmaceutical formulation is a solution formulation.

9. The device as claimed in claim 1, wherein the pharmaceutical formulation is a suspension formulation.

10. The device as claimed in claim 1, wherein the active ingredient is selected from beclomethasone dipropionate, budesonide, fluticasone propionate or mometasone furoate.

11. The device as claimed in claim 1, wherein the active ingredient is beclomethasone dipropionate.

12. The device as claimed in claim 1, wherein the vial further contains a co-solvent.

* * * * *